US012690803B2

(12) United States Patent
Ma et al.

(10) Patent No.: US 12,690,803 B2
(45) Date of Patent: Jul. 28, 2026

(54) METHOD AND SYSTEM FOR EARLY DIAGNOSIS OF PARKINSON'S DISEASE BASED ON MULTIMODAL DEEP LEARNING

(71) Applicant: Shandong University, Jinan (CN)

(72) Inventors: Xin Ma, Jinan (CN); Cuihua Lv, Jinan (CN)

(73) Assignee: Shandong University, Jinan City (CN)

( * ) Notice: Subject to any disclaimer, the term of this patent is extended or adjusted under 35 U.S.C. 154(b) by 0 days.

(21) Appl. No.: 19/027,045

(22) Filed: Jan. 17, 2025

(65) Prior Publication Data

US 2025/0213174 A1     Jul. 3, 2025

(30) Foreign Application Priority Data

Jan. 18, 2024    (CN) ........................ 202410080108.X

(51) Int. Cl.
 *A61B 5/00*         (2006.01)
 *G06T 7/00*         (2017.01)
        (Continued)

(52) U.S. Cl.
 CPC .......... *A61B 5/4082* (2013.01); *A61B 5/4803* (2013.01); *G06T 7/0012* (2013.01); *G06V 10/44* (2022.01); *G06V 10/62* (2022.01); *G06V 10/764* (2022.01); *G06V 10/774* (2022.01); *G06V 10/82* (2022.01); *G06V 40/171* (2022.01); *G10L 25/30* (2013.01); *G10L 25/66* (2013.01); *G16H 50/20* (2018.01); *G06T 2207/10016* (2013.01);
        (Continued)

(58) Field of Classification Search
 CPC ... A61B 5/4082; A61B 5/4803; A61B 5/7257; A61B 5/7267; G06T 2207/10016; G06T 2207/20081; G06T 2207/20084; G06T 2207/30201; G06T 7/0012; G06V 10/44; G06V 10/62; G06V 10/764; G06V 10/774; G06V 10/806; G06V 10/82; G06V 40/171; G10L 25/18; G10L 25/30; G10L 25/66; G16H 50/20; Y02T 10/40
 See application file for complete search history.

(56) References Cited

U.S. PATENT DOCUMENTS

2022/0280098 A1 *  9/2022  Hao ..................... A61B 5/0004
2023/0172526 A1 *  6/2023  Lipsmeier .............. G10L 15/22

FOREIGN PATENT DOCUMENTS

CN        111553899 A     8/2020
CN        111680541 A     9/2020
        (Continued)

*Primary Examiner* — Mark D Remaly

(57)            ABSTRACT
A method for early diagnosis of Parkinson's disease based on multimodal deep learning is provided. Audio-visual data of a to-be-diagnosed subject while performing a speech task is acquired. The audio-visual data are preprocessed to extract a plurality of audio segments and a plurality of video segments. A face image sequence is extracted from each of the plurality of video segments. A Mel-spectrogram of each of the plurality of audio segments is calculated. The face image sequence and the Mel-spectrogram are input into a multimodal deep learning model to output a classification result for Parkinson's disease early diagnosis of the to-be-diagnosed subject. A system for early diagnosis of Parkinson's disease based on multimodal deep learning is also provided.

6 Claims, 9 Drawing Sheets

(51) Int. Cl.

| | | |
|---|---|---|
| *G06V 10/44* | (2022.01) | |
| *G06V 10/62* | (2022.01) | |
| *G06V 10/764* | (2022.01) | |
| *G06V 10/774* | (2022.01) | |
| *G06V 10/82* | (2022.01) | |
| *G06V 40/16* | (2022.01) | |
| *G10L 25/30* | (2013.01) | |
| *G10L 25/66* | (2013.01) | |
| *G16H 50/20* | (2018.01) | |

(52) U.S. Cl.
CPC ............... *G06T 2207/20081* (2013.01); *G06T 2207/20084* (2013.01); *G06T 2207/30201* (2013.01)

(56) References Cited

FOREIGN PATENT DOCUMENTS

| CN | 113317763 A | 8/2021 |
|---|---|---|
| CN | 114519809 A | 5/2022 |
| CN | 115620356 A | 1/2023 |

* cited by examiner

METHOD AND SYSTEM FOR EARLY DIAGNOSIS OF PARKINSON'S DISEASE BASED ON MULTIMODAL DEEP LEARNING

CROSS-REFERENCE TO RELATED APPLICATIONS

This application claims the benefit of priority from Chinese Patent Application No. 202410080108.X, filed on Jan. 18, 2024. The content of the aforementioned application, including any intervening amendments made thereto, is incorporated herein by reference in its entirety.

TECHNICAL FIELD

This application relates to artificial intelligence-assisted disease diagnosis and diagnosis technology, and more particularly to a method and system for early diagnosis of Parkinson's disease based on multimodal deep learning.

BACKGROUND

Parkinson's disease (PD) is the second most prevalent neurodegenerative disease after Alzheimer's disease, which primarily affects the motor control area, with clinical symptoms such as resting tremor, bradykinesia, and reduced facial expressions. It is estimated that up to 90% of PD patients experience hypokinetic dysarthria, which is characterized by reduced speech volume, inaccurate consonants, concentrated vowels, and changes in speech rate accompanied by involuntary facial movements. The dysarthria is not only one of the most common orofacial symptoms of PD, but also one of the earliest symptoms. These early manifestations before the onset of muscle rigidity, resting tremor, gait abnormalities, or slow movements make speech signals a valuable biomarker for early diagnosis of PD. However, the clinical assessment of PD-related language disorders relies significantly on subjective assessments by neurologists and speech-language pathologists using rating scales based on experience. This subjective method has a certain degree of dependency and lacks reliable objective tools, which makes the accurate assessment of hypokinetic dysarthria in PD patients a challenging and urgent issue.

In recent years, the automatic recognition and analysis of audio-visual information has made great progress in computer vision research. This method has achieved remarkable results in the fields of emotion recognition, medical applications, audio enhancement and event prediction by analyzing audio features from different dimensions. At present, considering the hypokinetic dysarthria of PD patients, the deep learning-based automatic audio-visual information recognition technology can effectively and objectively evaluate and assist diagnosis by analyzing the condition of PD patients through audio. However, this method still has some problems, such as the contradiction that the effectiveness of the auxiliary diagnosis system greatly depends on the existence of large-scale and high-quality data, while the existing PD dysarthria dataset is small in scale. Moreover, the main limitation of the current research is that it only focuses on audio data. The signal of a single modality limits the final analysis results, resulting in inaccurate final results.

SUMMARY

In order to address the deficiencies in the prior art, the present disclosure provides a method and system for early diagnosis of Parkinson's disease based on multimodal deep learning, which adopts an audio-visual fusion to combine convolutional neural network (CNN) technology with a cross-attention mechanism to construct a multimodal deep learning model specifically for evaluating dysarthria in Parkinson's disease patients. Fusion analysis of video and voice modality signals can more effectively capture audio-visual features, thereby significantly improving the accuracy of early diagnosis of Parkinson's disease and assisting doctors in diagnosis based on diagnosis and classification results. In addition, integration of large amounts of audio and visual data can improve the diagnosis effectiveness.

In order to achieve the above object, the following technical solutions are adopted.

In a first aspect, this application provides a method for early diagnosis of Parkinson's disease based on multimodal deep learning, comprising:

(1) acquiring audio-visual data of a to-be-diagnosed subject while performing a speech task;

(2) preprocessing the audio-visual data to extract a plurality of audio segments and a plurality of video segments, wherein each of the plurality of audio segments corresponds to a synchronized one among the plurality of video segments; extracting a face image sequence from each of the plurality of video segments; and calculating a Mel-spectrogram of each of the plurality of audio segments; and (3) inputting the face image sequence and the Mel-spectrogram into a multimodal deep learning model to output a classification result for Parkinson's disease early diagnosis of the to-be-diagnosed subject, wherein the multimodal deep learning model comprises a local feature extraction module, an audio feature extraction module, a feedforward network and a cross-attention module;

wherein step (3) is performed through steps of:

(3.1) extracting visual features from the face image sequence through the local feature extraction module, and extracting audio features from the Mel-spectrogram through the audio feature extraction module; and (3.2) inputting the visual features and the audio features to the feedforward network, and inputting the visual features and the audio features to the cross-attention module to learn a cross-modal attention weight; performing feature fusion on the visual features and the audio features based on the cross-modal attention weight to obtain multimodal features; and outputting the classification result based on the multimodal features.

In a second aspect, this application provides a system for early diagnosis of Parkinson's disease based on multimodal deep learning, comprising:

a data acquisition module;

a data preprocessing module; and a diagnosis module;

wherein the data acquisition module is configured to acquire audio-visual data of a to-be-diagnosed subject while performing a speech task;

the data preprocessing module is configured to preprocess the audio-visual data to extract a plurality of audio segments and a plurality of video segments, extract a face image sequence from each of the plurality of video segments, and calculate a Mel-spectrogram of each of the plurality of audio segments; and each of the plurality of audio segments corresponds to a synchronized one among the plurality of video segments;

the diagnosis module comprises a multimodal deep learning model; and the diagnosis module is configured to input the face image sequence and the Mel-spectrogram into a multimodal deep learning model to output a classification result for Parkinson's disease early diagnosis of the to-be-diagnosed subject; and the multimodal deep learning model comprises a local feature extraction module, an audio feature extraction module, a feedforward network and a cross-attention module; the multimodal deep learning model is configured to extract visual features from the face image sequence through the local feature extraction module, extract audio features from the Mel-spectrogram through the audio feature extraction module, input the visual features and the audio features to the feedforward network, and input the visual features and the audio features to the cross-attention module to learn a cross-modal attention weight, perform feature fusion on the visual features and the audio features based on the cross-modal attention weight to obtain multimodal features, and output the classification result based on the multimodal features.

In a third aspect, this application provides an electronic device, comprising:

a memory;

a processor; and a computer instruction executable by the processor;

wherein the computer instruction is configured to be stored in the memory, and the processor is configured to execute the computer instruction to implement the above method.

In a fourth aspect, this application provides a non-transitory computer-readable storage medium, wherein a computer instruction is stored on the non-transitory computer-readable storage medium; and the computer instruction is configured to be executed by a processor to implement the above method.

Compared to the prior art, the present disclosure has the following beneficial effects.

The present disclosure provides a method and system for early diagnosis of Parkinson's disease based on multimodal deep learning, which not only constructs a comprehensive audio-visual fusion dataset, i.e., the Chinese Parkinson's disease audio-visual dataset (CPD-AVD), but also propose an end-to-end fusion multimodal deep learning framework (i.e., the multimodal deep learning model). Auditory and visual cues are comprehensively considered, and the cross-attention module is adopted to synergistically combine local visual information with spectrogram-based audio features, thereby enhancing the ability to recognize subtle differences in audio related to Parkinson's disease, significantly improving the accuracy of Parkinson's disease early diagnosis. This is conducive to assisting doctors in detecting disease symptoms as early as possible, conducting comprehensive treatment, and enabling doctors to understand the dynamics of the patient's disease progression in real time.

BRIEF DESCRIPTION OF THE DRAWINGS

The accompanying drawings constituting a part of this application are intended to provide a further understanding of the present disclosure. The embodiments of the present disclosure and descriptions thereof are intended to explain the present disclosure, and are not intended to limit the scope of the present disclosure.

FIGS. 2*a*-*b* show Mel-spectrograms generated based on an audio segment in accordance with an embodiment of the present disclosure;

DETAILED DESCRIPTION OF EMBODIMENTS

Figure 1:
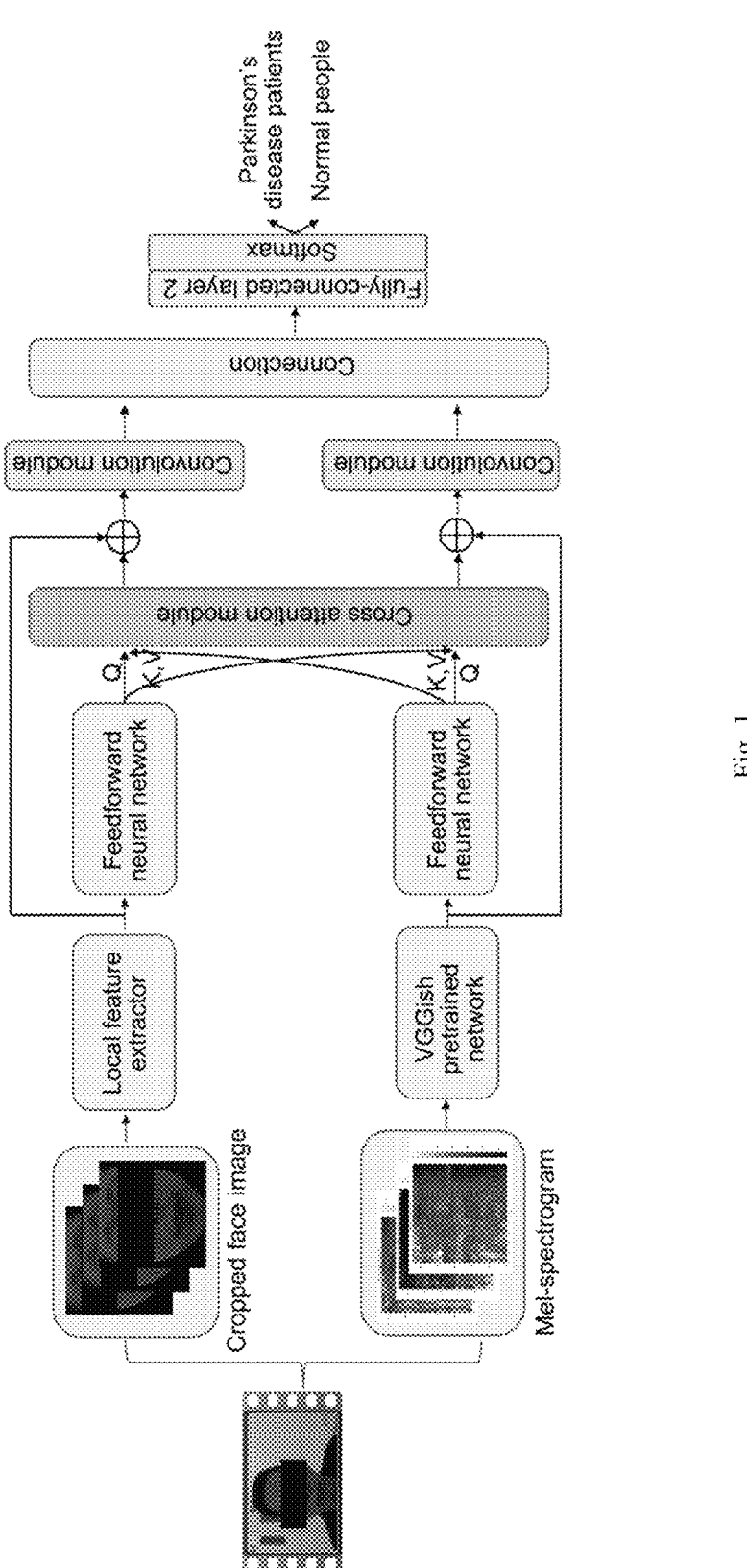
FIG. 1 schematically shows a network of a multimodal deep learning model in accordance with an embodiment of the present disclosure.

The present disclosure will be further described below with reference to the embodiments and accompanying drawings. It should be noted that the embodiments disclosed herein are merely illustrative of the disclosure, and are not intended to limit the present disclosure. Unless otherwise defined, technical or scientific terms used herein shall have the same meaning as commonly understood by those of ordinary skill in the art to which this application belongs. In addition, it should be understood that terms "comprise" and/or "include" used herein are intended to indicate the presence of features, steps, operations, devices, components and/or combinations thereof.

Embodiment 1

The existing technical solutions for early detection and auxiliary diagnosis of Parkinson's disease (PD) based on audio data have the problem that the amount of data affects the effectiveness of diagnosis and that only focusing on audio data of a single modality leads to poor diagnostic accuracy. In view of the limitations of data sets and methods in the prior art, in this embodiment, different types of audio-visual samples are collected from a large number of PD patients and healthy participants for multi-type speech tasks. This takes into account that the hypokinetic speech circuit damage of PD leads to abnormal pronunciation and changes in pronunciation morphology, which are usually manifested as involuntary or slow lip movements and muscle stiffness in the perioral area. These observable changes can be reflected through visual data, which also emphasizes the potential of fusing visual and audio data. Therefore, the present disclosure integrates audio-visual information to understand the pathological characteristics of PD more comprehensively, thereby improving the detection accuracy. On this basis, a multimodal deep learning model for audio-visual fusion is proposed in this embodiment, which combines convolutional neural network technology with a cross-attention mechanism. The multimodal deep learning model integrates two branches for extracting visual features and audio Mel-spectrogram features, and fuses the visual features and audio features through a cross-attention module to effectively learn the complementary information between visual and audio features, resulting in more comprehensive multimodal fusion features. The above audiovisual fusion method greatly improves the accuracy of PD diagnosis, which is superior to traditional machine learning and deep learning methods for early diagnosis of PD, and has a more efficient fusion of visual and voice data than using only voice signals.

The PD early diagnosis method based on multimodal deep learning provided herein has the following beneficial effects.

Firstly, a Chinese Parkinson's disease Audiovisual Comprehensive Dataset (CPD-AVD) is constructed, which includes audiovisual data of 130 PD patients and 90 healthy subjects performing speech tasks, addressing the main limitations of existing PD dysarthria datasets. This dataset not only significantly expands the sample size, but also integrates audio and visual data, thus filling a key gap in multimodal research on PD.

Secondly, the audio-visual fusion multimodal deep learning framework used herein has a unique dual-branch structure, which can extract visual features and audio Mel-spectrogram features related to PD. The audio-visual fusion multimodal deep learning framework further enhances the audio-visual fusion effect through the cross-attention mechanism, which aims to more effectively capture audio features, thereby significantly improving the accuracy of the PD diagnosis model.

Provided herein is a method for early diagnosis of PD based on multimodal deep learning, which includes the following steps.

(1) Audio-visual data of a to-be-diagnosed subject while performing a speech task is acquired.

(2) The audio-visual data is preprocessed to extract a plurality of audio segments and a plurality of video segments, where each of the plurality of audio segments corresponds to a synchronized one among the plurality of video segments. A face image sequence is extracted from each of the plurality of video segments. A Mel-spectrogram of each of the plurality of audio segments is calculated.

(3) The face image sequence and the Mel-spectrogram are input into a multimodal deep learning model to output a classification result for PD early diagnosis of the to-be-diagnosed subject. The multimodal deep learning model includes a local feature extraction module, an audio feature extraction module, a feedforward network and a cross-attention module.

The method in this embodiment will be described in detail below.

As early dysarthria is a prominent symptom in PD patients, early auxiliary diagnosis can be facilitated by integrating visual and audio information to provide a comprehensive assessment.

(S1) Data acquisition and preprocessing

Specifically, the audio-visual data of the to-be-diagnosed subject while performing the speech task is acquired and preprocessed to extract the plurality of audio segments and the plurality of video segments, where each of the plurality of audio segments corresponds to a synchronized one among the plurality of video segments. The face image sequence is extracted from each of the plurality of video segments. The Mel-spectrogram of each of the plurality of audio segments is calculated.

Firstly, in order to assess the participants' dysarthria, various speech tasks are designed, including number recitation, sentence reading and spontaneous audio. The number recitation includes counting from 1 to 10 and then counting from 10 to 1 in reverse to assess pronunciation and cognitive ability. The sentence reading requires the participants to read a set of short sentences in order to analyze the clarity and rhythm of continuous audio. The spontaneous audio is to let the participants discuss personal topics such as hobbies, family and career, thereby eliciting natural language responses. The to-be-diagnosed subject is asked to perform the above speech tasks, and the corresponding audio-visual data are obtained using a camera during the execution of the tasks.

Secondly, the acquired data are preprocessed. The audio-visual data (i.e., video files) are processed using a Fast Forward MPEG (FFmpeg) tool. An audio track and a video image are extracted from the video file and stored as separate files. The audio-visual data are then divided into segments with the same length, i.e., audio segments and video segments each lasting 3 s. For each 3-s segment, 30 evenly distributed frames are selected. Each video segment is a sequence of 30 video frame images.

A multi-task cascaded convolutional network (MTCNN) is a deep learning model for face detection. The MTCNN model is used to perform face recognition on the video frame sequence images in the video segments. After detection, the video frame sequence images are subjected to face cropping. The video frames are standardized to a resolution of 224× 224 pixels, and the face image sequence is extracted.

Figure 2A:
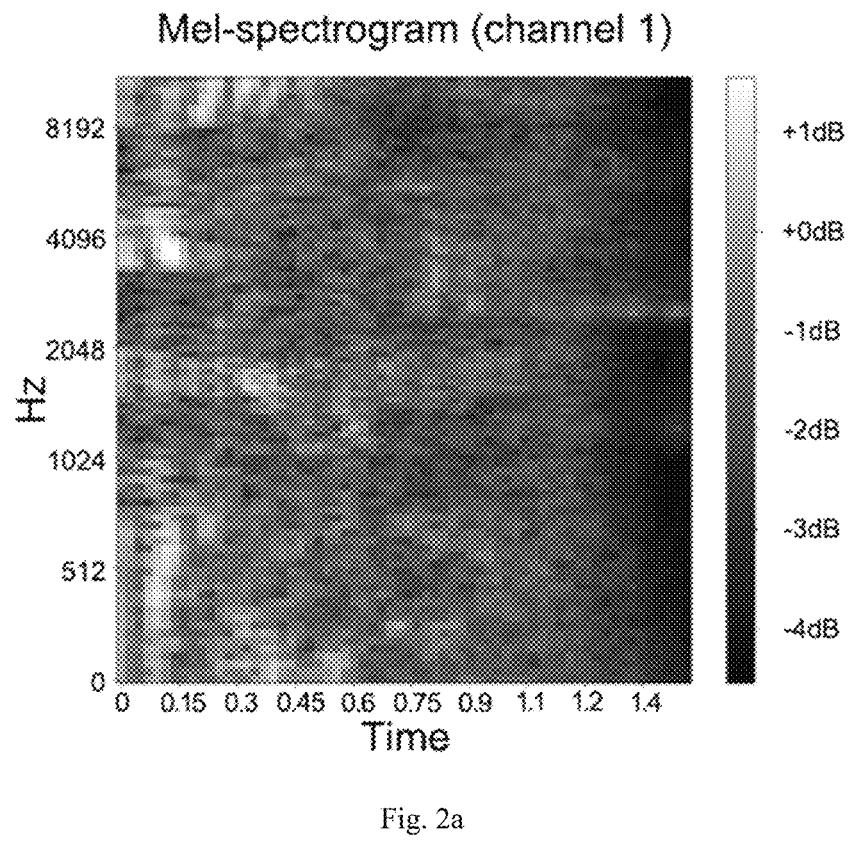
Figure 2B:
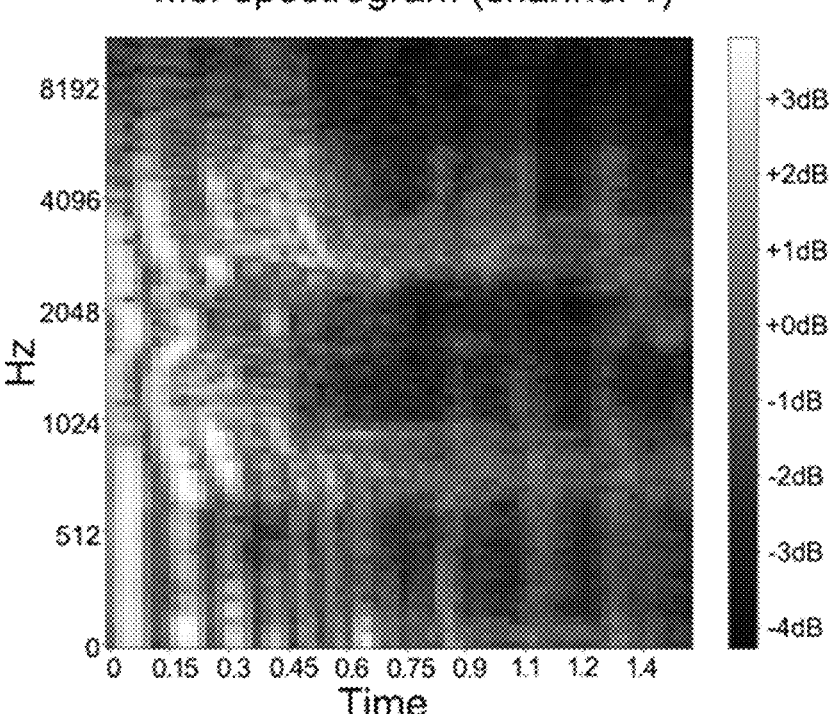

For the audio segments, the audio segment data is converted into a waveform audio file (WAV) for storage. In order to match the subsequent PD diagnosis model, the audio segment data is converted into the Mel-spectrogram. Unlike the short-time Fourier transform (STFT) spectrogram used in existing PD research, the reason for choosing the Mel-spectrogram is that it matches the auditory characteristics of the human ear. Specifically, a Hamming window with a set length of 25 ms is used to extract the amplitude spectrum for each audio signal with a frame shift of 10 ms. Then, a 64-band Mel filter bank is used for logarithmic transformation to calculate the Mel-spectrogram of the audio signal. As shown in FIGS. 2a-b, FIG. 2a is a Mel-spectrogram of a 59-year-old male PD patient, and FIG. 2b is a Mel-spectrogram of a 59-year-old male healthy control. Compared with the healthy control, the audio of the PD patient often shows more obvious vibrations or fluctuations, as well as irregular sound frequency changes. In terms of sound amplitude, the audio of the PD patient often exhibits greater fluctuations than that of the healthy control. In addition, the audio of the PD patient is usually less clear and has lower energy, resulting in lower amplitude shown in the Mel-spectrogram. Based on the observation of the Mel-spectrograms, the significant difference in audio characteristics between the PD patient and the healthy individual can be clearly observed. The auxiliary analysis and diagnosis adopting the Mel-spectrograms results in a better effect.

(S2) The face image sequence and the Mel-spectrogram are input into the multimodal deep learning model to output the classification result for PD early diagnosis of the to-be-diagnosed subject. In order to achieve better fusion of multimodal features, a multimodal fusion framework specifically for analyzing audio-visual data is adopted herein, that is, the multimodal deep learning model is constructed, as shown in FIG. 1. First, two independent feature extraction modules (i.e., visual feature extraction module and audio feature extraction module) are used to extract the visual features and the audio features, respectively. Next, correlations between the visual features and the audio features are calculated by using the cross-attention module to generate a fused feature representation. Finally, the fused features are input into a fully-connected layer, and final diagnosis and classification results are output through a Softmax layer used for classification tasks, that is, the to-be-diagnosed subject is identified as an individual with PD or a normal individual, so as to assist doctors in diagnosing PD.

(1) Visual Feature Extraction Module

The extraction of the visual features is done by a specially designed local feature extractor, which is divided into two main parts: a visual front-end network and a visual temporal network.

The visual front-end network adopts ShuffleNet-V2 as the core network and is added with a two-dimensional (2D) convolution module, which is configured to encode the video frame sequence into a frame-based embedding sequence. The main purpose of this network is to capture the detailed information of each frame image. The face image sequence $$X_v^{B \times C \times H \times W}$$

is input into the visual front-end network, where B represents the number of images in the face image sequence, C represents the number of channels, and H and W respectively represent a height and width of the face image. In this embodiment, B=30, C=3, and H=W=224. Specifically, the face image sequence first passes through a convolution module Conv1 to capture a global facial feature map $$F_{vg}^{B \times H' \times W' \times C'},$$

where H=W=56, and C=29. Then, the global facial feature map is spatially divided into four patches, and is subjected to local feature extraction using deep separable convolution modules, where the integration of the deep separable convolution modules can reduce the computational load of the model and enhance the ability to capture feature relationships. Finally, the four local feature maps are aggregated along a spatial axis to form a local facial feature $$F_{vlocal}^{B \times H \times W \times C}$$

with a feature dimension of [30,116,28,28]. Then, stage 2, stage 3 and Conv5 convolution modules are applied to perform average pooling to obtain the final visual feature representation $$F_{vlocal}^{B \times d},$$

where B=30 represents the time dimension, and d=1024 represents the feature dimension.

The visual temporal network is configured to learn and represent dynamic temporal features across consecutive frames. The visual temporal network consists of a video temporal convolution module, which includes a one-dimensional convolutional layer, a batch normalization layer, and a rectified linear unit (ReLU) with a residual connection. The visual temporal network can effectively capture facial motion features in different time intervals and extract visual features with temporal correlation, thereby obtaining a comprehensive representation of the temporal aspects of facial motion.

(2) Audio Feature Extraction Module

Figure 3:
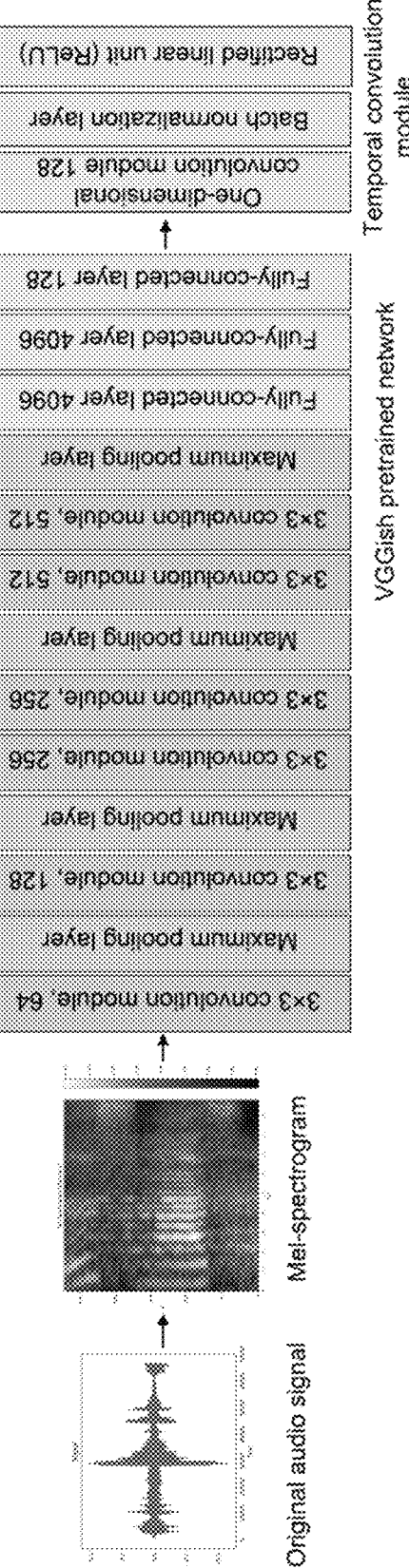
FIG. 3 is a structural diagram of an audio feature extraction module in accordance with an embodiment of the present disclosure.

In order to further refine the representation of the audio features, the audio feature extraction module adopts a VGGish network and is pretrained on a large AudioSet. The structure of the VGGish network is shown in FIG. 3, which facilitates the extraction of more detailed audio feature maps from the final convolution layer. In order to capture the temporal correlation in the audio data, the pretrained VGGish network is improved by introducing a temporal convolution module. The temporal convolution module includes a one-dimensional convolution, a batch normalization layer and a ReLU connected in sequence, which is configured to extract the audio features at different time intervals from the initially extracted audio data, thereby enhancing the ability to recognize temporal patterns in audio. The audio features extracted by means of the combination of the VGGish pretrained network and temporal convolution module are represented as $$F_a^{N \times d},$$

where N=3, and d=128. This audio feature extraction module can effectively improve the overall depth and robustness of the feature representation in the model.

(3) Cross-Modal Fusion Module (Including Feedforward Network and Cross-Attention Module)

In this embodiment, inspired by the Transformer-based method in the field of natural language processing, a cross-modal Transformer module is adopted in the framework to fuse the audio features and visual features. This module integrates multimodal inputs through a feedforward fusion process, adopts a pairwise cross-attention mechanism to explore the interaction between multimodal inputs, and acquires representations directly from aligned multimodal streams. In a case of non-aligned multimodal inputs, a one-dimensional temporal convolutional layer is configured as a preprocessor to align the inputs.

The cross-modal attention module is introduced in the feature layer to enhance the relationship between a target modality and other modalities. In this embodiment, in view of fusion, a multi-head attention mechanism is taken into account to capture complex relationships in the input data. Specifically, the visual features and audio features are allowed to learn the interaction between multimodal features by using a pairwise cross-attention mechanism. The visual features and audio features are allowed to pass through the feedforward network, respectively, to learn the cross-modal attention weight, and are subjected to feature fusion based on the cross-modal attention weight to obtain multimodal features.

Figure 4:
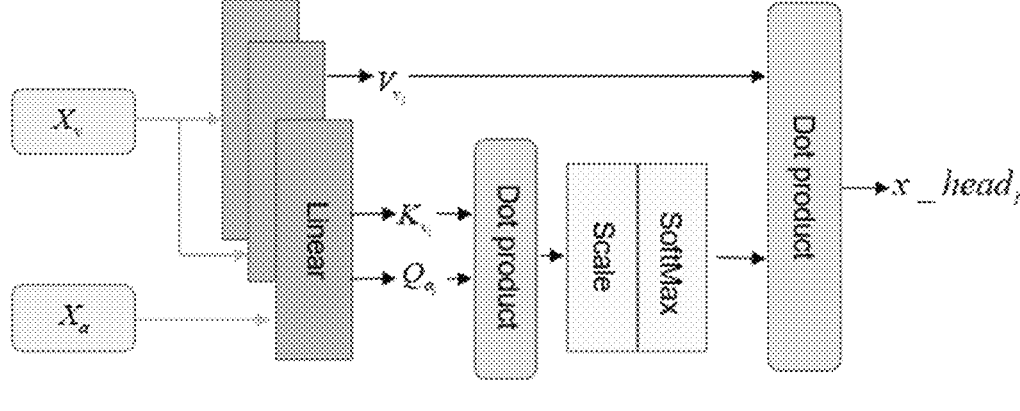
FIG. 4 is a structural diagram of a cross-attention module in accordance with an embodiment of the present disclosure.

In this embodiment, two modes are considered for the audio features and visual features corresponding to two modalities, and two cross-attention modules are thus adopted. Referring to a visually enhanced audio mode, the visual features and audio features are respectively converted into feature vectors in the same feature space through the feedforward network, that is, consistent in dimension. The audio features and the visual features are converted to the same dimension through the feedforward network, so that the model can subsequently learn the correlation between the two modalities and assign attention weights. FIG. 4 shows the operation of the attention head, where the embedded visual features are used as key vectors and value vectors, and the audio features are used as query vectors. The visual features and the audio features are input into the cross-attention module to learn the cross-audio-visual feature attention weights. Based on the learned cross-audio-visual feature attention weights, visual feature-enhanced audio features are obtained, which is output from the cross-attention module. The cross-attention module can be expressed as follows:

$$Q_{a_i} = X_{a_i}W_{Q_i}, K_{v_i} = X_{v_i}W_{K_i}, V_{v_i} = X_{v_i}W_{V_i} \qquad (1)$$

$$x\_head_i = softmax\left(\frac{Q_{a_i}K_{v_i}^T}{\sqrt{d}}\right)V_{v_i} \qquad (2)$$

$$h\_va = concat(x\_head_1, \dots, x\_head_h)W_o \qquad (3)$$

In Equations (1)-(3), $Q_{a_i}$ represents a query vector of an i-th attention head, $K_{v_i}$ represents a key vector of the i-th attention head, $V_{v_i}$ represents a value vector of the i-th attention head, and i=1, 2, 3, . . . , h; $X_{a_i}$ represents an audio embedded feature of the i-th attention head, and $X_{v_i}$ represents a visual embedded feature of the i-th attention head; W is a to-be-learned weight parameter, and D is a dimension of a feature vector; and h_va is an output of the cross-attention module, that is, a linear projection connecting outputs of all attention heads. Furthermore, in order to retain original information of the target modality and utilize the enhanced information from other modalities, a residual structure is introduced under the cross-modal attention mechanism, expressed as Equation (4):

$$X_{v-a} = LayNorm(Q_a + h\_va(Q_a, K_v, V_v)) \qquad (4)$$

In the Equation (4), LayNorm represents a regularization layer.

Similarly, the audio features and the visual features are input into the cross-attention module with the audio features as the key vectors and the value vectors and the visual features as the query vectors to learn the cross-modal attention weights. Audio feature-enhanced visual features are acquired based on the cross-audio-visual feature attention weights.

Finally, as shown in FIG. 1, the two modal features output by the cross-attention module (i.e., the visual feature-enhanced audio features and the audio feature-enhanced visual features) are fused with the corresponding original input features respectively. This feature fusion is performed to retain the original information of the target modality and simultaneously utilize the feature information enhanced by attention. The fused features corresponding to two modalities are concatenated after passing through the convolution module to obtain multimodal features. Based on the multimodal features, the final diagnosis and classification results are output through the fully-connected layer and the Softmax layer.

Furthermore, the above multimodal deep learning model is trained through the following process.

A plurality of sets of audio-visual data of a plurality of test subjects while performing the speech task are collected. Disease severity evaluation is performed according to the unified Parkinson's disease rating scale (UPDRS) to annotate and score the plurality of sets of audio-visual data. A training data set is constructed based on the plurality of sets of annotated audio-visual data. The plurality of test subjects include PD patients and healthy subjects.

In this embodiment, a CPD-AVD was constructed. The CPD-AVD includes audio and video recordings of 220 test subjects, including 130 PD patients with dysarthria (68 males, 62 females) and 90 healthy adults (37 males, 53 females). The recruitment of participants followed strict inclusion and exclusion criteria. The inclusion criteria required that the participants be over 50 years old, and have at least elementary school education; and for PD patients, they should be diagnosed by a professional neurologist. The exclusion criteria excluded patients with visual or hearing impairment, dementia or mental disorders, patients who had previous treatment including audio or language therapy, and other neurological diseases unrelated to PD. Participant demographics and other relevant information are shown in Table 1.

TABLE 1

| CPD-AVD participant demographics | | |
| --- | --- | --- |
| Variables | PD patients | Healthy control group |
| Number | 130 | 90 |
| Gender (male/female) | 68/62 | 37/53 |
| Age (mean/standard deviation) | 64.97/7.78 | 62.65/8.52 |

Clinical assessments of all patients were performed by experienced neurologists. Data collection focused on various aspects of the UPDRS-III, especially UPDRSIII-1, which assesses audio disorders on a scale of 0 (no audio problems) to 4 (severe audio disorders). In addition, the Hoehn-Yahr stage, which ranges from 0 (asymptomatic) to 4 (completely unable to take care of oneself), was recorded to track the progression of PD.

The above assessment participants were asked to perform speech tasks (including digital recitation, sentence reading and spontaneous audio, etc.), and the disease severity was assessed by experts based on the UPDRS-III. The plurality of sets of audio-visual data were annotated and scored. The CPD-AVD was constructed using the annotated audio-visual data as training samples.

Secondly, based on the training dataset, the multimodal deep learning model is trained using the cross-entropy loss and stochastic gradient descent (SGD) optimizer until the preset number of iterations is reached to complete the model training.

In order to evaluate the performance of the model, the proposed audio-visual model is applied to the CPD-AVD for experiments and compared with existing methods. Three widely recognized indicators are used here, which are accuracy, F1 score and sensitivity.

(1) According to the distribution of participants, the CPD-AVD is divided into a training subset, a validation subset and a test subset to ensure that each person only appears in one of the subsets, with a ratio of 7:2:1. The training of the model using the cross entropy loss and the SGD optimizer based on an initial learning rate is implemented in PyTorch. During training, various combinations of learning rate patience and learning rate step size, momentum and weight decay are used to implement the automatic learning rate adjustment strategy. All models are trained for 100 iterations. In order to improve the model's ability to learn the relationship between the two modalities, different hyperparameter combinations are set to train the model, as shown in Table 2.

TABLE 2

| Model hyperparameters | |
| --- | --- |
| Hyperparameters | Value |
| Initial learning rate | 0.01, 0.04 |
| Batch size | 8, 16 |
| Number of attention heads | 1, 2, 4, 8 |

The initial learning rate was set to 0.01 or 0.04; the accuracy was used as a monitoring indicator to execute the learning rate adjustment strategy; and the patience was set to 20. In addition, the model performance under different numbers of attention heads was experimented. The number of attention heads can adjust the model's ability to model the relationship between the audio mode and the visual mode, so that the interaction between the audio mode and the visual mode can be fully understood. It can be seen from Table 3 that the proportion of PD patients accurately predicted by the model increases in terms of sensitivity, but has a decreased overall performance in terms of F1 score. This result shows that in the presence of a large amount of data, increasing the number of attention heads is more likely to allow the model to learn general patterns between features, thereby improving performance; and in the case of samples with a small amount of data, the risk of model overfitting is increased. In this embodiment, considering the above factors, the initial learning rate=0.004, the batch size=8, and the number of attention heads=1 is selected as the optimal hyperparameter combination.

TABLE 3

| Model classification results with an initial learning rate of 0.04 | | | | | |
| --- | --- | --- | --- | --- | --- |
| Batch size | Number of attention heads | Learning rate | Accuracy/% | F1 score/% | Sensitivity/% |
| 8 | 1 | 0.004 | 92.68 | 94.23 | 96.08 |
| | 4 | 0.04 | 90.49 | 92.82 | 98.82 |
| | 8 | 0.04 | 90.24 | 92.54 | 97.25 |
| 16 | 1 | 0.004 | 92.44 | 94.05 | 96.08 |
| | 4 | 0.04 | 90.48 | 92.63 | 96.08 |
| | 8 | 0.04 | 89.27 | 91.94 | 98.43 |

Figure 5A:
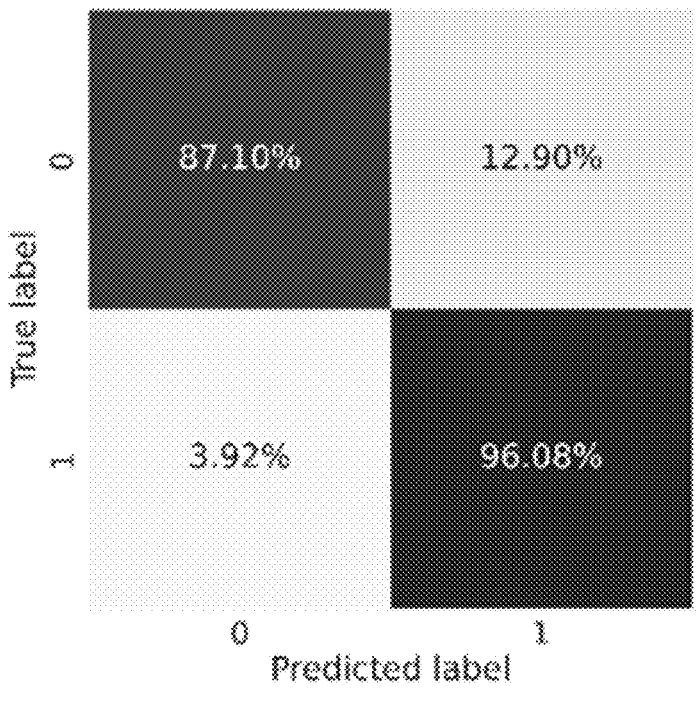
FIG. 5*a* shows a confusion matrix obtained by using an optimal model in a data testing phase in accordance with an embodiment of the present disclosure.
Figure 5B:
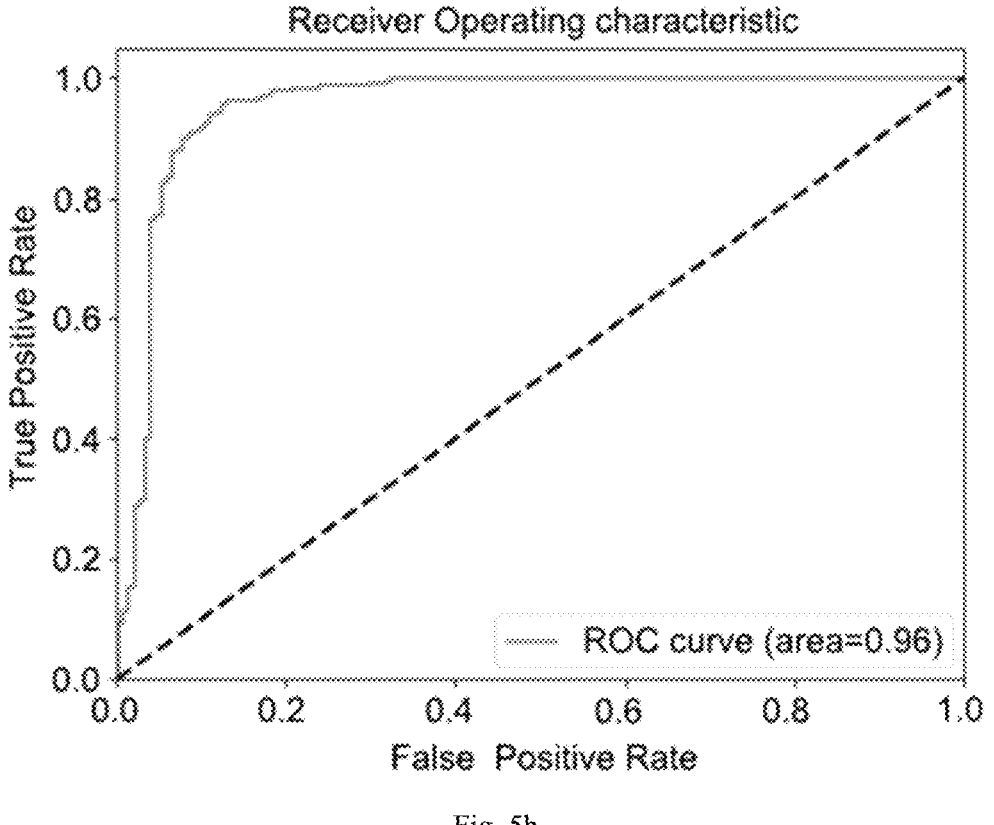
FIG. 5*b* shows a receiver operating characteristic (ROC) curve obtained by using the optimal model in the data testing phase in accordance with an embodiment of the present disclosure.

FIG. 5a shows a confusion matrix obtained in the data testing phase using the best model, and FIG. 5b shows the corresponding receiver operating characteristic (ROC) curve. The ROC-AUC (area under the ROC curve) is 0.96, indicating that the model has a strong ability to distinguish PD patients from healthy individuals. The confusion matrix shows that the accuracy of the model in PD recognition is 96.08%, and the accuracy in healthy control (HC) recognition is 87.10%. Although the accuracy of HC recognition is slightly lower than that of PD recognition, for auxiliary diagnosis tasks, the proposed model mainly plays a preliminary screening role, focusing on minimizing missed diagnoses. In this case, this model achieves effective results, which is consistent with the main goal of this embodiment, i.e., to improve the efficiency of PD diagnosis.

(2) In addition, in order to evaluate the role of visual information in dysarthria assessment, ablation experiments were also performed, which only focused on the audio modality, allowing a direct comparison of classification performance when visual data is ignored.

Specifically, traditional machine learning models based on expert features are adopted as baseline methods and are applied to the CPD-AVD. Hyperparameters of these models are shown in Table 4, where unspecified parameters default to the settings provided by Scikit-learn.

TABLE 4

| Machine learning model hyperparameters | |
| --- | --- |
| Machine learning model | Parameters |
| Support vector machine (SVM) | Kernel function = linear function, polynomial function, radial basis function, sigmoid function |
| Random forest (RF) | Number of trees = 30, 50, 70, 100 |
| Multilayer perceptron (MLP) | Hidden layer size = (8,), (16,), (32,) |

Two widely recognized and state-of-the-art toolboxes, Praat: doing phonetics by computer (Praat) and Open Source Speech and Music Interpretation by Large-space Extraction (OpenSMILE), were used to compare audio features associated with PD. That is, 18 features, including jitter, shimmer, harmonics, pitch and other derived acoustic measurements, were automatically extracted from the audio dataset using a Praat script. A Geneva Minimum Acoustic Parameter Set (EGeMAPS) was extracted from the audio recording using an OpenSMILE toolbox. This set of features including frequency-related features, energy/amplitude properties and spectral properties and statistical measurements obtained from these features ultimately form a comprehensive set of 88 dimensions.

Figure 6A:
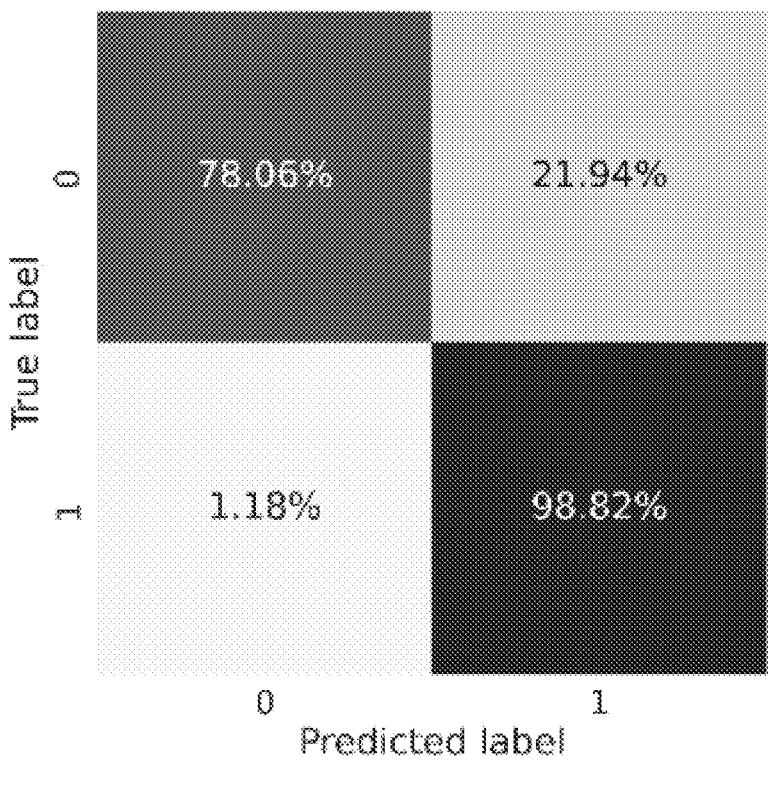
FIG. 6*a* shows a confusion matrix obtained by using an audio information-based model in the data testing phase in accordance with an embodiment of the present disclosure.
Figure 6B:
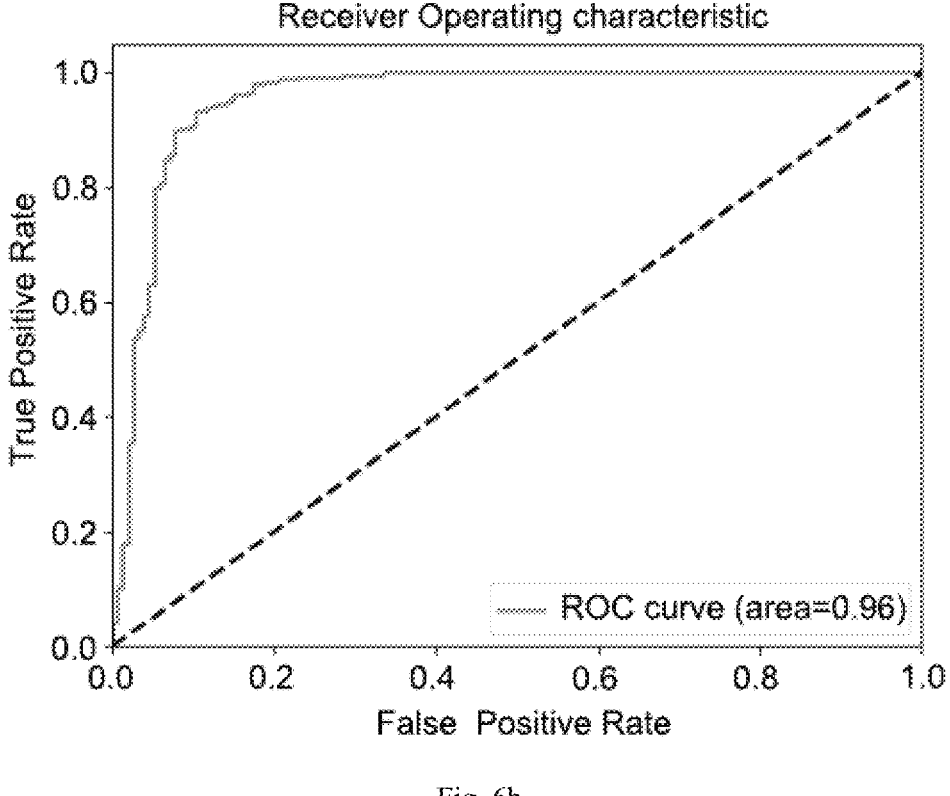
FIG. 6*b* shows a ROC curve obtained by using the audio information-based model in the data testing phase in accordance with an embodiment of the present disclosure.

The final experimental results are shown in Table 5. In a case where visual information is excluded and only audio information is used, the accuracy and sensitivity reach 90.97% and 98.82% respectively, and the confusion matrix and corresponding ROC-AUC curve are shown in FIGS. 6a-b. Confusion matrix analysis shows that the classification performance of normal individuals based solely on audio information is poor, which is 78.06%. This may be because the acoustic features extracted from audio are more indicative of PD. After adding visual cues, the recognition accuracy of healthy individuals increased to 87.1%. This further confirms the hypothesis that visual information provides key information for evaluating PD dysarthria, thereby verifying the effectiveness of the method proposed herein.

TABLE 5

| Classification results of the audio-visual fusion model and the audio-only modality model | | | |
| --- | --- | --- | --- |
| Models | Accuracy/% | F1 score/% | Sensitivity/% |
| Audio-only modality model | 90.97 | 93.16 | 98.82 |
| Audio-visual fusion model | 92.68 | 94.23 | 96.08 |

Table 6 shows the best results achieved by the traditional machine learning models with audio features as input. The results show that the support vector machine (SVM) model using the EGeMAPS feature set has the highest accuracy, with an accuracy and sensitivity of 79.26% and 74.93%, respectively. However, compared with the method proposed in this embodiment, these scores were reduced by 13.42% and 21.25%, respectively. The results show that extracting deep features from audio spectrograms can reveal important information about PD patients. Therefore, the deep learning method provided herein is more effective than manually extracting a limited set of features.

TABLE 6

Experimental results of traditional machine learning model

| Feature set | Decision model | Accuracy/% | F1 score/% | Sensitivity/% |
|---|---|---|---|---|
| 18-dimensional | MLP | 74.09 | 71.08 | 70.43 |
| feature set | RF | 78.23 | 76.07 | 75.23 |
| | SVM | 71.69 | 68.66 | 68.17 |
| EGeMAPS | MLP | 77.54 | 73.03 | 72.15 |
| | RF | 73.32 | 69.09 | 68.59 |
| | SVM | 79.26 | 76.09 | 74.93 |

The method provided in this embodiment solves the limitations of the current data set and proposes an audio-visual fusion deep learning framework, which utilizes the complex interaction between visual cues and audio features, adopts a dual-branch structure and cross-attention mechanism, and integrates multiple data modalities, so as to improve the diagnosis accuracy of early PD.

Embodiment 2

Provided herein is a system for early diagnosis of PD based on multimodal deep learning, including a data acquisition module, a data preprocessing module, and a diagnosis module.

The data acquisition module is configured to acquire audio-visual data of a to-be-diagnosed subject while performing a speech task.

The data preprocessing module is configured to preprocess the audio-visual data to extract a plurality of audio segments and a plurality of video segments, extract a face image sequence from each of the plurality of video segments, and calculate a Mel-spectrogram of each of the plurality of audio segments; and each of the plurality of audio segments corresponds to a synchronized one among the plurality of video segments.

The diagnosis module includes a multimodal deep learning model, and is configured to input the face image sequence and the Mel-spectrogram into the multimodal deep learning model to output a classification result for PD early diagnosis of the to-be-diagnosed subject. The multimodal deep learning model includes a local feature extraction module, an audio feature extraction module, a feedforward network and a cross-attention module. The multimodal deep learning model is configured to extract visual features from the face image sequence through the local feature extraction module, extract audio features from the Mel-spectrogram through the audio feature extraction module, input the visual features and the audio features to the feedforward network by means of a pairwise cross-attention mechanism, and input the visual features and the audio features to the cross-attention module to learn a cross-modal attention weight, perform feature fusion on the visual features and the audio features based on the cross-modal attention weight to obtain multimodal features, and output the classification result based on the multimodal features.

Embodiment 3

Provided herein is an electronic device, including a memory, a processor and a computer instruction executable by the processor. The computer instruction is configured to be stored in the memory, and the processor is configured to execute the computer instruction to implement steps in the method for early diagnosis of PD based on the multimodal deep learning.

Embodiment 4

Provided herein is a non-transitory computer-readable storage medium. A computer instruction is stored on the non-transitory computer-readable storage medium. The computer instruction is configured to be executed by a processor to implement steps in the method for early diagnosis of PD based on the multimodal deep learning.

The steps involved in Embodiments 2 to 4 correspond to the method in Embodiment 1, which can be implemented referring to the relevant description of Embodiment 1. The term "computer-readable storage medium" should be understood as a single medium or multiple media including one or more instruction sets; and should also be understood to include any medium that can store, encode or carry an instruction set for execution by a processor and executable by the processor to implement the method in the present disclosure.

Those of ordinary skill in the art should understand that the modules or steps of the present disclosure can be implemented by a general-purpose computer device. Alternatively, they can be implemented by a program code executable by a computing device, so that they can be stored in a storage device and executed by the computing device, or they can be made into individual integrated circuit modules, or multiple modules or steps can be made into a single integrated circuit module for implementation. The present disclosure is not limited to any specific combination of hardware and software.

The embodiments described above are merely illustrative of the present application, and are not intended to limit the scope of the present application. It should be understood that based on the embodiments in the present disclosure, various modifications or variations made by those of ordinary skill in the art without making creative efforts shall fall within the scope of the present disclosure.

What is claimed is:

1. A method for early diagnosis of Parkinson's disease based on multimodal deep learning, comprising:

(1) acquiring audio-visual data of a to-be-diagnosed subject while performing a speech task;

(2) preprocessing the audio-visual data to extract a plurality of audio segments and a plurality of video segments, wherein each of the plurality of audio segments corresponds to a synchronized one among the plurality of video segments; extracting a face image sequence from each of the plurality of video segments; and calculating a Mel-spectrogram of each of the plurality of audio segments; and (3) inputting the face image sequence and the Mel-spectrogram into a multimodal deep learning model to output a classification result for Parkinson's disease early diagnosis of the to-be-diagnosed subject, wherein the multimodal deep learning model comprises a local feature extraction module, an audio feature extraction module, a feedforward network and a cross-attention module;

wherein step (3) is performed through steps of:

(3.1) extracting visual features from the face image sequence through the local feature extraction module, and extracting audio features from the Mel-spectrogram through the audio feature extraction module; and (3.2) inputting the visual features and the audio features to the feedforward network, and inputting the visual features and the audio features to the cross-attention module to learn a cross-modal attention weight; performing feature fusion on the visual features and the audio features based on the cross-modal attention weight to obtain multimodal features; and outputting the classification result based on the multimodal features.

2. The method of claim 1, wherein the local feature extraction module comprises a visual front-end network and a visual temporal network;

the visual front-end network is based on ShuffleNet-V2, and further comprises a two-dimensional (2D) convolution module; the visual front-end network is configured to encode the face image sequence into a frame-based embedding sequence; and the visual temporal network consists of a video temporal convolution module, and is configured to capture facial motion visual features in different time intervals; and the step of extracting the visual features from the face image sequence through the local feature extraction module comprises:

extracting facial visual features from each frame of the face image sequence through the visual front-end network, and extracting the visual features from the facial visual features through the visual temporal network, wherein the visual features are time-correlated.

3. The method of claim 1, wherein the audio feature extraction module is a VGGish network provided with a convolution module; the audio feature extraction module is configured to extract the audio features at different time intervals from the plurality of audio segments; and the step of extracting the audio features from the Mel-spectrogram through the audio feature extraction module comprises:

inputting the Mel-spectrogram into the audio feature extraction module, and extracting the audio features through the VGGish network, wherein the audio features are time-correlated.

4. The method of claim 1, wherein step (3.2) comprises:

after the visual features and the audio features pass through the feedforward network, inputting the visual features and the audio features into the cross-attention module with the visual features as key vectors and value vectors and the audio features as query vectors to learn the cross-modal attention weight, and acquiring visual feature-enhanced audio features based on the cross-modal attention weight; and inputting the visual features and the audio features into the cross-attention module with the audio features as the key vectors and the value vectors and the visual features as the query vectors to learn the cross-modal attention weight, and acquiring audio feature-enhanced visual features based on the cross-modal attention weight; and fusing the visual feature-enhanced audio features with the audio features to obtain first fused features, and fusing the audio feature-enhanced visual features with the visual features to obtain second fused features, and concatenating the first fused features with the second fused features to obtain the multimodal features.

5. The method of claim 1, wherein the multimodal deep learning model is trained through steps of:

collecting a plurality of sets of audio-visual data of a plurality of test subjects while performing the speech task, wherein the plurality of test subjects comprise Parkinson's disease patients and healthy subjects; performing disease severity evaluation according to a unified Parkinson's disease rating scale (UPDRS) to annotate and score the plurality of sets of audio-visual data; and constructing a training data set based on the plurality of sets of annotated audio-visual data; and based on the training data set, training the multimodal deep learning model by means of a cross-entropy loss and a stochastic gradient descent optimizer until a preset number of iterations is reached.

6. A non-transitory computer-readable storage medium, wherein a computer instruction is stored on the non-transitory computer-readable storage medium; and the computer instruction is configured to be executed by a processor to implement the method of claim 1.

* * * * *